United States Patent [19]

Cheng et al.

[11] 4,071,427

[45] Jan. 31, 1978

[54] ARSENITE ELECTRODE

[75] Inventors: Kuang Lu Cheng, Kansas City, Mo.; Eric En-Kuang Chao, Waterloo, Canada

[73] Assignee: Curators of the University of Missouri, Columbia, Mo.

[21] Appl. No.: 742,597

[22] Filed: Nov. 17, 1976

[51] Int. Cl.² ............................................. G01N 27/46
[52] U.S. Cl. ................................. 204/195 M; 204/1 T
[58] Field of Search ....................... 204/195 M, 195 G

[56] References Cited

U.S. PATENT DOCUMENTS

| | | | |
|---|---|---|---|
| 3,563,874 | 2/1971 | Ross et al. | 204/195 M |
| 3,591,464 | 7/1971 | Frant et al. | 204/195 M |
| 3,672,962 | 6/1972 | Frant et al. | 204/195 M |
| 3,709,813 | 1/1973 | Johnson et al. | 204/195 G |
| 3,809,636 | 5/1974 | Higashiyama et al. | 204/195 M |
| 3,821,100 | 6/1974 | Hilton et al. | 204/195 G |
| 3,822,199 | 7/1974 | Luck et al. | 204/195 M |

*Primary Examiner*—T. Tung

[57] ABSTRACT

An electrode sensitive to arsenite ions in solution, the ion-sensitive portion being an imporous membrane of silver arsenite and silver sulfide.

8 Claims, 2 Drawing Figures

ARSENITE ELECTRODE

BACKGROUND OF INVENTION

1. Field of Invention

This invention relates to electrochemical detection and measurement of arsenite ions in solution.

2. Prior Art

Presently, quantitative determinations of arsenite ions are made by iodimetric titration or spectrographic procedures. These methods do not lend themselves readily to continuous, real-time monitoring and usually require sampling.

A commercial arsenite ion selective electrode has been manufactured by Sensorex Incorporated, Irving, Calif., but its construction has not been published in the literature.

SUMMARY OF INVENTION

The present invention contemplates a specific ion electrode for qualitatively and quantitatively determining the activity of arsenic ions in solution.

Further objects of the present invention are to provide an electrode which permits direct on-stream monitoring of arsenite ion activity; to provide such an electrode which yields a continuous signal output voltage having a simple logarithmic relation to arsenite ion activity with sufficiently fast response time to permit readings to be made substantially in real time; to provide such an electrode which is rugged and in which the ion-sensitive portion or element is a solid-state membrane; and to provide an electrode of the type described sensitive to arsenite ions in a stable and reproducible manner substantially free from interference from most other ions incuding hydrogen ion.

Yet other objects of the invention will in part be obvious and will in part appear hereinafter. The invention accordingly comprises the apparatus possessing the construction, combination of elements, and arrangement of parts, and comprises the several steps and the relation of one or more of such steps with respect to each of the others, all of which are exemplified in the following detailed disclosure, and the scope of the application of which will be indicated in the claims.

For a fuller understanding of the nature and objects of the present invention, reference should be had to the following detailed description taken in connection with the accompanying drawings wherein:

PREFERRED EMBODIMENT

Generally, the foregoing and other objects of the present invention are effected by providing an electrode having an ion-sensitive element in the form of a substantially imporous membrane of silver sulfide intimately and substantially uniformly mixed with silver arsenite, the membrane being substantially free of silver and of the metals of which the other compounds are formed, at least on the surface thereof intended to contact a solution under test. The presence of free metals in the membrane surfaces tends to make the corresponding electrode drifty and susceptible to interferences from redox couples that might exist in the sample solutions under test. Thus, electron transfer reactions of the type $Ag^- + e^- \rightarrow Ag$ and the like, are not pertinent to the present invention inasmuch as there is substantially no free metal present which will enter such reaction or act as a source or sink of electrons. The term "membrane" as used herein, consistent with its usual usage in potentiometric electrode technology, is intended to embrace a sheet-like structure, generally regardless of its flexibility or curvature, which primarily provides a pair of surfaces between which ionic charge transfer is effected.

Figure 1:
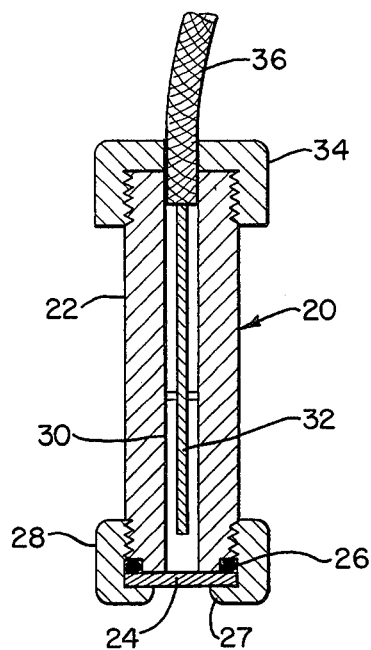
FIG. 1 shows a schematic, side-elevational, cross-sectional simplified view of an electrode embodying the principles of the present invention.

Referring now to the drawings there is shown in FIG. 1 electrode 20 embodying the principles of the present invention and comprising an elongated, hollow tubular container or stem 22 open at both ends. The stem typically is formed of a liquid impervious, substantially rigid, electrically insulating material, such as unplasticized polyvinylchloride, polytetrafluorethylene, glass or the like, substantially chemically inert to solutions being tested and with which the stem might be placed in contact.

One end of the stem 22 is capped or sealed with a barrier disc or membrane 24 which will be described in detail later herein. Membrane 24 can be quite thick, for example, $\frac{1}{4}$ inch, although thinner structures are preferred. Membrane 24 can be sealed across the one end of stem 22 with an appropriate sealing compound such as an epoxy resin, but advantageously, as shown, is mounted on O-ring 26 disposed about the periphery of the opening in the stem, and held in a pressed-fit against the O-ring by annular flange 27 of collar 28 threadedly mounted on the stem. When collar 28 is rotated in the proper direction, it advances axially, forcing membrane 24 in a tight fit against the O-ring, thus sealing the one end of stem 22. Both the O-ring and collar 28 are preferably made of a plastic material such as polyvinylchloride.

Disposed internally of stem 22 and in electrical and physical contact with the inner surface of the membrane 24 is charge transfer means providing a fixed concentration of silver either in metallic or ionic form. This means is shown as a reference electrolyte 30, for example, an aqueous saturated solution of various salts as described hereinafter. Immersed in electrolyte 30 is internal reference electrode 32, for example the well-known Ag-AgCl element. This combination of electrolyte 30 and reference electrode 32 provides means for electrically contacting the internal face (i.e., the surface of the membrane contacting the electrolyte) at a substantially stable or fixed potential.

The other open end of stem 22 is fitted with annular cap 34 having an aperture in which is sealed the usual coaxial cable 36, the central conductor of which is connected to internal reference electrode 32 and the peripheral conductor of which is intended to provide electrostatic shielding.

The more important considerations in fabricating the electrode of FIG. 1 lie in the structure of membrane 24. The other elements and the shape and size of the electrode are not particularly critical and can be selected according to the anticipated use.

Silver sulfide is unusual in that, not only is it highly insoluble in water ($K_{sp}$ $10^{-52}$) but in at least its low temperature (B) form has a relatively low electrical bulk-resistivity coupled with exceptionally high cationic conductivity, i.e., electrical conductivity through the silver sulfide crystal lattice is effected primarily by migration of silver ions instead of by a conduction mechanism involving ions or electrons.

The membrane of the present invention is formed of silver sulfide intimately and uniformly mixed with silver arsenite. The working range of mole percent of silver arsenite in silver sulfide is between 0.01% and 50%.

The following is an example of the preparation of the membranes used in the invention, and the responses of electrodes using such membranes. Where the response is noted as being Nernstian, it is intended to indicate that the ion-sensitive membrane responds substantially in accordance with the well-known Nernst equation in a stable and reproducible manner.

Arsenic trioxide, $As_2O_3$, in amounts indicated in Table I was dissolved in 100 ml of 0.2M sodium hydroxide solution. To this solution, $Na_2S - 9H_2O$, in amounts indicated in Table I, was added. The resulting solution was filtered and titrated with $AgNO_3$. A slight excess of $AgNO_3$ was added. The pH of the solution was controlled in the range of 8 to 12. After standing a few minutes, the supernatant liquid was decanted and washed with 200 ml of doubly deionized water approximately twenty times such that the solution showed no trace of $Ag^+$. The solution was filtered and dried overnight at 100° C. The resulting precipitate was silver sulfide containing a percentage of $Ag_3AsO_3$ as indicated in Table I.

Membranes were prepared with a diameter of 13 mm and a thickness of 0.5 - 0.8 mm by pressing at 15,000 p.s.i. the silver sulfide-silver arsenite mixture for fifteen minutes. The resulting pellets were a black, shiny color and quite hard.

TABLE I

| Mole % intended in the ppt. | | Amount added | Amount added |
|---|---|---|---|
| $Ag_3AsO_3$ | $Ag_2S$ | $Na_2S \cdot H_2O$ | $As_2O_3$ |
| 0% | 100% | 2.6116 g | 0 |
| .01% | 99.99% | Physically mixed. | |
| 0.1% | 99.9% | 2.4544 g | 0.0031 g |
| | | 9.99 mmoles | 0.005 mmoles |
| 1% | 99% | 2.4525 g | 0.0100 g |
| | | 9.9 mmoles | 0.05 mmoles |
| 10% | 90% | 2.2130 g | 2.0991 g |
| | | 9.0 mmoles | 0.5 mmoles |
| 50% | 50% | 0.0611 g | 0.3726 g |
| | | 3.6 mmoles | 1.8 mmoles |

The composition of each pellet and the corresponding characterization of the electrode response is set forth in Table II below:

TABLE II

| Mole % $Ag_3AsO_3$ | Mole % $Ag_2S$ | Response |
|---|---|---|
| 0% | 100% | Unstable. |
| .01% | 99.99% | Negative drifting. |
| .1% | 99.9% | Approximately Nernstian. |
| 1% | 99% | Approximately Nernstian. |
| 10% | 90% | Positive drifting. |
| 50% | 50% | Excessively low slope. |

In the above example, the pellet obtained was substantially dense and imporous.

It can be postulated that the operative mechanism is as follows:

A membrane of $Ag_2S/Ag_3AsO_3$ separating two solutions, one of which is a reference solution containing $Ag^+$ at a fixed concentration and the other of which is a sample solution under test, will develop a potential $E_m$ according to the well-known Nernst equation.

$$E_m = C + RT/F \ln (Ag^+) \quad (1)$$

Where C, R, T, and F are all the usual well-known values and where $(Ag^+)$ is the silver ion activity in the test sample solution. Since $Ag_3AsO_3$ is more soluble than $Ag_2S$, the silver ion activity $(Ag^+)$ can be related to the arsenite activity $(AsO_3^{-3})$ through the solubility product $K_{(sp)}$ of $Ag_3AsO_3$ as follows:

$$(Ag^+)^3 = K(sp)/(AsO_3^{-3}) \quad (2)$$

Substituting Equation 2 into Equation 1 and simplifying $$E_m = C + RT/3F \ln [K(sp)/(AsO_3^{-3})] \quad (3)$$

Further simplifying $$E_m = C' - RT/3F \ln (AsO_3^{-3}) \quad (4)$$

The responses of the electrodes in a logarithmic manner substantially according to Equation 4 are obtained in practice in the following usual manner.

Figure 2:
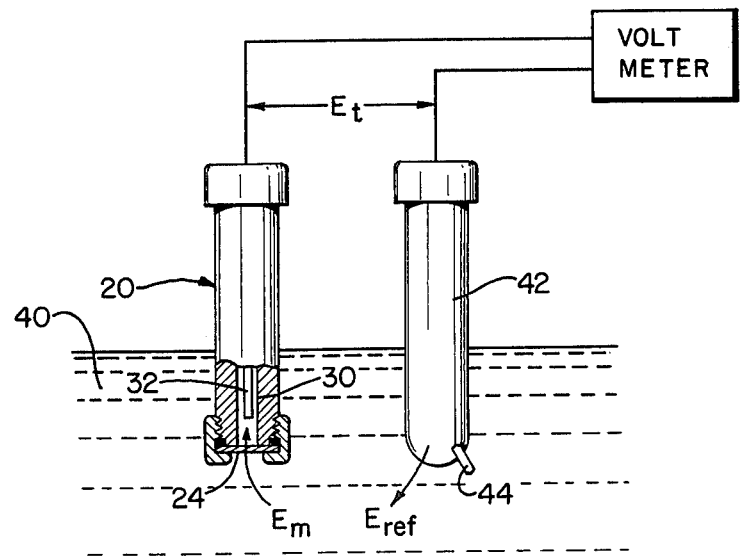
FIG. 2 is a schematic, side-elevational view, partly in cross-section of a cell employing the electrode of FIG. 1 for the detection of arsenite ions.

As shown in FIG. 2, electrode 20 of the present invention in use is placed so that the outer surface of membrane 24 contacts solution 40 under test (i.e., which contains the arsenite ions to be detected). A standard reference electrode 42 is also placed in contact with solution 40.

Electrode 42 typically is the usual assembly housed in a conventional glass shell containing an Ag-AgCl electrode in saturated KCl-AgCl separated by an asbestos fiber junction from a 1 M NaOH solution. The latter solution occupies the lower end of the shell and is coupled to solution 40 through the usual fiber junction shown at 44. Both electrode 20 and electrode 42 are connected electrically to respective inputs of electrometric device 46, the latter being preferably the usual high-input impedance voltmeter.

In operation of the assembly of FIG. 2, a potential, $E_{ref}$ of substantially fixed value (assuming constant temperature conditions) develops between reference electrode 42 and solution 40 independently of the ion concentration in the latter. Another potential, $E_m$, will develop across membrane 24 between internal electrolyte 30 and solution 40 in accordance with Equation 3. Because the potential, $E_{int}$, between reference electrode 32 and electrolyte 30 is also fixed, the total potential $E_t$, appearing between electrodes 42 and 20 will be the sum of $E_m$, $E_{ref}$ and $E_{int}$, and thus varies with $E_m$ only. $E_t$ can be readily measured on electrometric device 46, thus indicating the presence and activity of the desired ions in solution 42. An example of such measurement is as follows:

An electrode, formed as described and incorporating a membrane of 0.1% $Ag_3AsO_3$/99.9% $Ag_2S$ was used to measure activities of $AsO_3^{-3}$ in a number of aqueous solutions of different, precisely serially, diluted concentrations. The solutions all contained a background of 1M $NaNO_3$ and 0.1M $Na_2HPO_4 \cdot 7H_2O$ to fix the pH and maintain a constant ionic strength. Typically all potentials are as follows for each solution of different concentration:

| Conc. of $AsO_3^{-3}$ (moles/liter) | Response in mv |
|---|---|
| $1 \times 10^{-2}$ | 84 |
| $1 \times 10^{-3}$ | 121 |
| $1 \times 10^{-4}$ | 156 |

-continued

| Conc. of $AsO_3^{-3}$ (moles/liter) | Response in mv |
| --- | --- |
| $1 \times 10^{-5}$ | 184 |
| $1 \times 10^{-6}$ | 196 |
| $1 \times 10^{-7}$ | 198 |

Since certain changes may be made in the above apparatus and method without departing from the scope of the invention herein involved, it is intended that all matter contained in the above description or shown in the accompanying drawing shall be interpreted in an illustrative and not in a limiting sense.

What is claimed is:

1. In an electrode for potentiometric determination of the activity of ions in solution, an element sensitive to arsenite ions comprising a membrane of a mixture of $Ag_2S$ and $Ag_3AsO_3$.

2. An element as defined in claim 1 wherein said membrane is substantially free of silver.

3. An element as defined in claim 1 wherein said membrane is substantially imporous.

4. An element as defined in claim 1 wherein said $Ag_3AsO_3$ is in proportion to said $Ag_2S$ in an optimum range of ratios, expressed in mole percentages, of between 1:9999 and 1:9.

5. A potentiometric system for measuring the activity of arsenite ions in a solution with a reference electrode and an ion-sensitive electrode both contacting said solution and connected to a potential measuring device, wherein said ion-sensitive electrode has as the ion-sensitive element thereof, a membrane of a mixture of $Ag_2S$ and $Ag_3AsO_3$.

6. A potentiometric system as defined in claim 5 wherein said membrane is substantially free of silver.

7. A potentiometric system as defined in claim 5 wherein said membrane is substantially imporous.

8. A potentiometric system as defined in claim 5 wherein said $Ag_3AsO_3$ is in proportion to said $Ag_2S$ in an optimum range of ratios, expressed in mole percentages, of between 1:9999 and 1:9.

* * * * *